United States Patent [19]

Wilk

[11] 3,951,622
[45] Apr. 20, 1976

[54] TIME RELEASE PERFUME METHOD AND DEVICE

[76] Inventor: Immanuel J. Wilk, 1044 Noel Drive, Menlo Park, Calif. 94025

[22] Filed: Dec. 4, 1974

[21] Appl. No.: 529,372

[52] U.S. Cl. ................................. 55/16; 55/158; 206/439; 206/823
[51] Int. Cl.² ........................................ B01D 59/12
[58] Field of Search ............... 55/16, 158, 384, 387; 206/439, 823

[56] References Cited
UNITED STATES PATENTS

| | | | |
|---|---|---|---|
| 2,732,092 | 1/1956 | Lawrence | 55/158 X |
| 3,032,182 | 3/1962 | Bachtolm | 206/439 X |
| 3,449,266 | 6/1969 | Cashman et al. | 206/823 X |
| 3,598,122 | 8/1971 | Zaffaroni | 128/268 |
| 3,598,123 | 8/1971 | Zaffaroni | 128/268 |
| 3,706,410 | 12/1972 | Baker | 55/384 X |

Primary Examiner—John Adee
Attorney, Agent, or Firm—Phillips, Moore, Weissenberger, Lempio & Strabala

[57] ABSTRACT

The invention is concerned with a method and device for the time release of a fragrance such as a perfume, the odor of the fragrance released being substantially unchanged from the odor of the original fragrance. The fragrance is sealed or otherwise enclosed within a container at least one portion of which comprises a permeable membrane of polyethylene or polypropylene, the membrane having a thickness of no more than about 6 mils (0.01524 cm), the fragrance including a top note, a middle note, an end note and alcohol (such as ethanol) having a molecular weight below 100. Fragrance components slowly pass through the membrane so as to provide an odor adjacent the membrane which is unchanged from the odor of the fragrance within the container.

12 Claims, 4 Drawing Figures

U.S. Patent    April 20, 1976    3,951,622
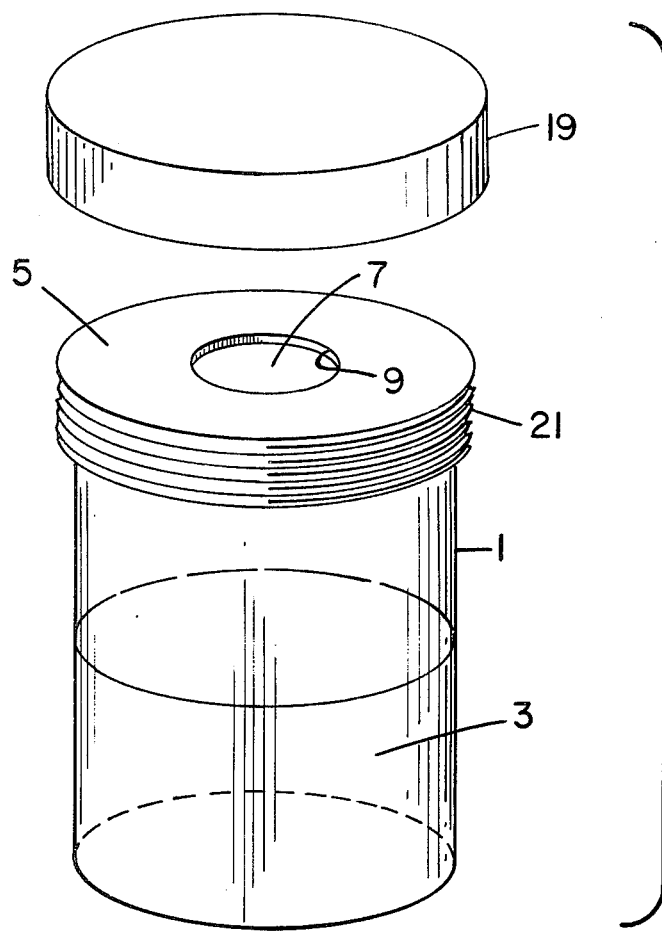
FIG_1
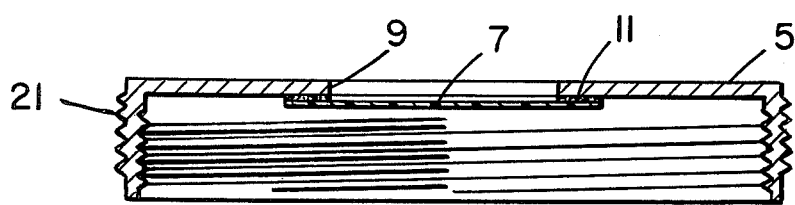
FIG_2
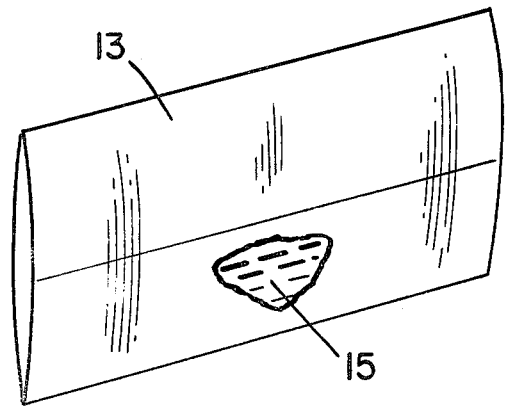
FIG_3
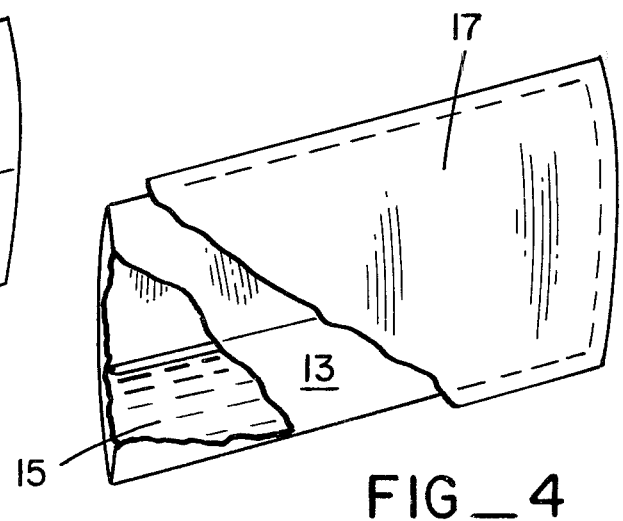
FIG_4

TIME RELEASE PERFUME METHOD AND DEVICE

BACKGROUND OF THE INVENTION

The invention is concerned with a novel and advantageous device and method for the time release of a fragrance.

Typically, a fragrance, e.g., a perfume, is applied to the body or clothing of the user where it evaporates relatively quickly providing a high odor level due to its top note component immediately after application. The odor level then drops off and rather rapidly changes to first a middle note odor and later an end note odor. The fragrance can, of course, be damaging to some types of fabrics by staining them or otherwise causing them to deteriorate. Also, the relatively high initial odor followed by the fairly fast drop-off and the above mentioned changes in odor are not desirable since it would be better if the fragrance odor lasted at a constant level and remained unchanged for a long period of time, thus more efficiently making use of the fragrance and maintaining unchanged the odor selected by the user.

Presently fragrances are sometimes absorbed on porous solid materials to provide time release of their odors. This type of a time release device, however, has a disadvantage in that when it sits against clothing, relatively high concentration of the fragrance will tend to pass out of the fragrance-impregnated material and into the clothing. Thus, staining or other damage to the fabric can occur and an unduly high level of fragrance can be introduced into the clothing. Further, the absorbed fragrance either changes odor just as does a fragrance applied to clothing or to the body or a fragrance which is substantially all one note is used to eliminate odor changes.

DESCRIPTION OF THE PRIOR ART

Fragrances such as perfumes are blends of odorous components. A complete perfume is generally blended from three mixtures of different volatility. The most volatile mixture is referred to in the trade as a "top note"; the next most volatile mixture as a "middle note"; and the least volatile mixture as an "end note". As stated, each of the notes is itself a mixture and hence a complete perfume is a complex mixture of three notes plus, usually, ethanol. It is, of course, possible to prepare a perfume from any number of individual components or mixtures but the final resulting blend, for attractive perfumes, is equivalent to a blend of the three notes. The compositions of a number of typical perfumes can be found in the book, "Practice of Modern Perfumery" by Dr. Paul Jellinek, Interscience Publishers, Inc., New York (1954) on pages 50–79.

The prior art discloses that any number of organic chemicals pass through permeable membranes such as polyethylene and polypropylene membranes. In fact, the prior art teaches a number of processes for separating organic chemicals which processes take advantage of the fact that different organic chemicals exhibit different diffusion coefficients with respect to various membranes. Relevant in this regard are U.S. Pat. Nos. 2,953,502; 2,960,462; 2,984,623; 3,062,905; 3,370,102; 3,494,862; and 3,429,104.

In view of the extensive prior art teachings that membranes are useful for the separation of organic chemicals from one another and of the further fact that the top note, middle note and end note mixtures of perfumes normally spontaneously separate from one another at room temperature when exposed to air, it is indeed surprising that a particularly defined permeable membrane of particular thickness is useful for the time release of a highly complex mixture of organic compounds (a fragrance) in such a manner that the components of the fragrance which pass through the membrane exhibit the same odor as does the fragrance itself. And this is true even though some components of the fragrance might by themselves not pass through the membrane. And even though, indeed, some of the components of the fragrance might normally be solids at ambient temperatures.

SUMMARY OF THE INVENTION

The device of the present invention is adapted to uniformly and over a long period of time release the unchanged odor of a fragrance. The device comprises a container, at least one portion of which comprises a permeable membrance selected from the group consisting of polyethylene, polypropylene, copolymers and mixtures thereof, said membrane having a thickness of no mcre than about 6 mils (0.01524 cm), said container having fully enclosed therein a mixture of mutually soluble fragrance components, corresponding to top note, middle note and end note fractions, the membrane being permeable to at least one of the components, said components including an essential oil and an alcohol having a molecular weight below 100, any other portion of said container being substantially impermeable to the mixture.

The method of the invention is a method for uniformly releasing the unchanged odor of a fragrance over a long period of time. The method comprises fully enclosing a fragrance comprising a mixture of mutually soluble fragrance components corresponding to top note, middle note, and end note fractions including an essential oil and an alcohol having a molecular weight below 100 within a container at least one portion of which comprises a permeable membrane selected from the group consisting of polyethylene, polypropylene, copolymers and mixtures thereof, said membrane having a thickness of no more than about 6 mil, whereby the components of said mixture diffuse through said membrane without significant fractionation thereof to produce an odor externally of said container which is substantially unchanged from the odor of the mixture, any other portion of said container being substantially impermeable to said mixture.

BRIEF DESCRIPTION OF THE DRAWING

FIG. 1 illustrates in perspective one embodiment of the present invention.

FIG. 2 illustrates a detail in the construction of the embodiment illustrated in FIG. 1.

FIG. 3 illustrates in perspective another embodiment of the present invention.

FIG. 4 illustrates in partially cut away perspective yet another embodiment of the present invention.

DESCRIPTION OF THE PREFERRED EMBODIMENT

Referring first to FIG. 1, there is illustrated a glass bottle 1 having therein a fragrance, in particular a perfume, 3. A hard fragrance impermeable plastic lid 5 is also illustrated screwed onto the top of the glass bottle. The lid includes a permeable polyethylene membrane 7 attached over a hole 9 which passes therethrough. Attachment of the polyethylene membrane is via a sealant material 11 which may be glue or the like as illustrated in FIG. 2. Since the glass bottle and the lid are both impermeable to passage of the perfume components in any reasonable period of time, these components can only pass through the membrane.

FIG. 3 illustrates a polyethylene envelope 13 filled with a liquid 15 which again comprises a perfume. In this case the permeable membrane comprises the entire container for the perfume. The perfume components diffuse out through the envelope 13 so that they can be smelled externally of the envelope.

FIG. 4 illustrates an embodiment wherein the envelope 13, which is fully or partially filled with the liquid 15, is surrounded by a perfume impervious package, in particular a bag 17 which separates the envelope from the surrounding atmosphere. Since the bag is impervious to perfume mixtures, the embodiment of FIG. 4 is storable for long periods of time without loss of perfume. Odor is thus only detectable after the bag has been opened. It is clear that a perfume impervious package is usable also with the embodiment illustrated in FIG. 1. A perfume impervious cap 19 can be provided to removably fit over the lid 5. The cap 19 can be of the snap on variety or it can be threaded and appropriate mating threads 21 can be provided on the lid 5. With the cap 19 in place, loss of perfume is prevented.

Since the fragrance containers of the invention are each completely sealed, only tearing, puncturing or breaking of the containers will rapidly release the liquid. Hence, clothing and the like is relatively safe from damage.

It is essential and critical to the practice of the present invention that the fragrance within the container include an essential oil and an alcohol having a molecular weight below 100. When the fragrance satisfies these criteria then the odor which passes through the membrane will be substantially unchanged from the odor of the liquid fragrance itself. That is, the odor will not change as it passes through the membranes and will include top note, middle note and end note fractions in substantially the same concentration as the fragrance within the container. This is an extremely surprising result since membranes are well-known to separate organic liquids. Further it is essential that the membrane is permeable to at least one of the components of the fragrance. Although the theory of operation of the method and device of the present invention are not fully understood, it has been found that when each of the above criteria are followed then the odor adjacent the membrane externally of the container will be substantially the unchanged odor of the fragrance contained within the container.

A number of fragrances are known. These include perfume; disinfectants - deodorants, such as phenolics or terpene - terpinol types; insecticides - pesticides, such as pyrethrins; and water treatment chemicals, such as certain compounds containing chlorine.

Fragrances such as perfumes, as is well-known, are a complex mixture of tens and more often hundreds or even thousands of components. The raw material for perfumes include essential oils, flower oils, natural extracts such as Myrrh resin; gums; balsams; beans; mosses and other plants; animal fixatives, e.g. ambergris, and musk; aromatics, e.g. fatty and other alcohols, aldehydes, esters, ketones, indole, phenolic aldehydes, terpenes, vanillin; prepared blends consisting of artificial flower oils, e.g. rose or fancy bases and the like.

Essential oils are generally mixtures of terpenes and other hydrocarbons. They lower the solubility of oils in ethanol. They may include oxygenated compounds referred to in the trade as osmophors, e.g., alcohols, aldehydes, ketones, esters, acids, acetals, oxides, lactones, and phenols. They are responsible for the specific odor of the oils and also are the more ethanol soluble portion. Also included in essential oils are nitrogen compounds, e.g. indoles, anthranilates, cyanides, amines, quinolines, pyridines, pyrazines, pyrroles and the like but these are less frequent and have more intensive odors. Further present in essential oils are sulphur compounds in minor quantities. These have even more pronounced odors than do the nitrogen compounds. Typical sulphur compounds would include mustard, garlic, onion oils and the like. Rose oil, for example, has 221 constituents, bergamot oil about 35 ingredients, lime oil about 155 ingredients, lavender oil about 40 ingredients. Orange oil contains about 96% d-limonene, and aniseed oil contains about 19% anethole.

Detailed definitions of perfumes and essential oils can be found in the Kirk-Othmer Encyclopedia of Chemical Technology, Second Edition, Intrascience, New York, 1967. Reference may particularly be had to Volume 14 of this work, pages 178 to 216 for description of essential oils and to Volume 14, pages 717 to 746 for descriptions of perfumes.

The preferred alcohol having molecular weight below 100 is ethanol. Ethanol is preferred because of its cost, odor and ready availability. The ethanol passes through the container just as do the other components of the fragrance and in such a concentration that the odor of the fragrance externally of the membrane is substantially unchanged from the odor of the liquid fragrance containing the ethanol. This is somewhat surprising since polyethylene bottles are often used for long term storage of ethanol without apparent loss therefrom.

Further, it is essential that the permeable membrane be selected from the group consisting of polyethylene, polypropylene, copolymers and mixtures thereof and be of a thickness of no more than about 6 mils. If the material is other than polyethylene, polypropylene, copolymers and mixtures thereof, the odor adjacent the membrane exteriorly of the container will be changed from the odor of the fragrance contained within the container. Also, if the membrane is thicker than about 6 mils, the odor will be changed, fractionation evidently occurring as the components of the fragrance pass through the thicker membrane. The only lower limit on the thickness of the membrane is that it be thick enough to provide sufficient strength and to assure that fractionation of the top note, middle note and end note components does not occur as it would if no membrane was present. Also, polyethylene is the preferred membrane material since it is relatively inexpensive and excellent results have been realized in releasing the unchanged odor of a fragrance when utilizing this particular membrane material. The 6 mils limitation on thickness refers most particularly to low density polyethylene. For high density polyethylene, the thickness is generally somewhat less than with low density polyethylene.

For best results, it is preferred that the essential oil includes a terpenoid hydrocarbon. It has been found that in the presence of terpenoid hydrocarbons the odor released through the membrane is quite unchanged from the odor of the liquid fragrance contained within the container.

The invention will be better understood by reference to the following illustrative example.

EXAMPLE

In this example, a sample of an ethanol solution of a fragrance was divided into three aliquots while a portion of the fragrance was retained as a control for later odor comparison in an impermeable glass bottle. The fragrance was a perfume which included top note, middle note and end note parts. The fragrance included a terpene containing essential oils. Each of the aliquots was separately sealed into a low density polyethylene envelope. The following table summarizes the results of the experiment.

| Membrane Thickness | | Time Odor First Detected | Time Odor Attained Full Strength Odor of Control | Duration of Test, Weeks | Comparison with Odor of Original Fragrance |
|---|---|---|---|---|---|
| Mils | cm | | | | |
| 2 | 0.00508 | 13 minutes | 38 minutes | 10 | Same |
| 4 | 0.01016 | 30 minutes | 20 hours | 14 | Same |
| 6 | 0.01524 | 2 days | did not | — | Different |

The above data clearly indicate that with membranes having a thickness of less than about 6 mils (0.01524 cm) the odor permeating the membranes is the same as the odor of the original fragrance and that this identity of odors continued for at least 10 weeks. Since the odor of the 6 mil envelope never was the same as that of the fragrance sealed therein, the time (Duration of Test) for which the odors remained the same could not be measured.

It is immediately apparent from examination of the Table that the device and method of the present invention are effective to provide time release of the substantially unchanged odor of a perfume over significantly long periods of time and that by using thicker membranes a lower but longer lasting odor results than when using thinner membranes.

while the invention has been described in connection with specific embodiments thereof, it will be understood that it is capable of further modification, and this application is intended to cover any variations, uses or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

That which is claimed is:

1. A device which uniformly and over a long period of time releases the unchanged odor of a fragrance, comprising:
   a container, at least one portion of which comprises a membrane selected from the group consisting of polyethylene, polypropylene, copolymers and mixtures thereof, said membrane having a thickness of no more than about 6 mils, said container having fully enclosed therein a mixture of mutually soluble fragrance components, the membrane being permeable to at least one of said components, said components including an essential oil and an alcohol having a molecular weight below 100.

2. A device as in claim 1, further characterized in that said fragrance comprises a perfume including a top note, a middle note and an end note fraction.

3. A device as in claim 2, further characterized in that said essential oil includes a terpenoid hydrocarbon.

4. A device as in claim 3, further characterized in that said alcohol comprises ethanol.

5. A device as in claim 4, further characterized in that said membrane comprises polyethylene.

6. A device as in claim 1, including a fragrance impermeable package separating said one portion and the atmosphere adjacent and external of said container.

7. A method for uniformly releasing the unchanged odor of a perfume over a long period of time, comprising:
   fully enclosing a fragrance comprising a mixture of mutually soluble fragrance components including an essential oil and an alcohol having a molecular weight below 100 within a container at least one portion of which comprises a membrane selected from the group consisting of polyethylene, polypropylene, copolymers and mixtures thereof, said membrane having a thickness of no more than about 6 mil whereby the components of said mixture diffuse through said membrane without significant fractionation thereof to produce an odor externally of said container which is unchanged from the odor of the fragrance.

8. A method as in claim 7, wherein said fragrance comprises a perfume including a top note, a middle note and an end note fraction.

9. A method as in claim 8 further characterized in that said essential oil includes a terpenoid hydrocarbon.

10. A method as in claim 9, further characterized in that said alcohol comprises ethanol.

11. A method as in claim 10, further characterized in that said membrane comprises polyethylene.

12. A method as in claim 7, including as an added step, surrounding said one portion with a package which is substantially impervious to the components of said fragrance.

* * * * *